(12) United States Patent
Vie et al.

(10) Patent No.: US 7,393,380 B2
(45) Date of Patent: Jul. 1, 2008

(54) METHOD OF GUARANTEEING AT LEAST ONE CHARACTERISTIC OF A FLUID USED FOR PRODUCING FOOD PRODUCTS

(75) Inventors: Jean-François Vie, Versailles (FR); Henry Ledon, Versailles (FR); Philippe Girardon, Versailles (FR); Christel Girault, Voisins le Bretonneux (FR)

(73) Assignee: L'Air Liquide, Societe Anonyme A Directoire et Conseil de Surveillance pour l'Etude et l'Exploitation des Procedes Georges Claude, Paris (FR)

( * ) Notice: Subject to any disclaimer, the term of this patent is extended or adjusted under 35 U.S.C. 154(b) by 430 days.

(21) Appl. No.: 10/497,931

(22) PCT Filed: Dec. 4, 2002

(86) PCT No.: PCT/FR02/04174

§ 371 (c)(1),
(2), (4) Date: Dec. 20, 2004

(87) PCT Pub. No.: WO03/048875

PCT Pub. Date: Jun. 12, 2003

(65) Prior Publication Data

US 2005/0106062 A1 May 19, 2005

(30) Foreign Application Priority Data

Dec. 6, 2001 (FR) .................................. 01 15787

(51) Int. Cl.
*B01D 53/02* (2006.01)
*G05B 1/00* (2006.01)
*A61L 2/00* (2006.01)

(52) U.S. Cl. ........................... 95/8; 95/1; 95/11; 95/90; 95/278; 96/109; 96/111; 96/112; 96/113; 96/417; 96/419; 96/422; 210/662; 210/670; 210/739; 210/85

(58) Field of Classification Search ........................ 95/1, 95/8, 11, 90, 96, 106, 267, 273, 278, 900; 96/108, 109, 110, 111, 112, 113, 114, 417, 96/419, 420, 421, 422, 418; 210/661, 662, 210/670, 690, 739, 767, 787, 85, 188
See application file for complete search history.

(56) References Cited

U.S. PATENT DOCUMENTS 3,879,129 A * 4/1975 Inoue .......................... 356/335

(Continued)

FOREIGN PATENT DOCUMENTS

EP 0 584 747 A1 8/1993

(Continued)

*Primary Examiner*—Jason M. Greene
(74) *Attorney, Agent, or Firm*—Christopher J. Cronin (57) ABSTRACT

A method for guaranteeing at least one characteristic of a fluid used for producing food products. This method utilizes a system for piping and delivering the fluid, combined with means for producing the products, in order to use the fluid for producing the products; the measuring a value of the characteristic; the comparing the measured value with a predetermined threshold value; the act of executing an action if the measured value departs from the threshold value; the combining the measured value with first information for identifying at least one product; and then the storing the associated value and the associated information.

14 Claims, 4 Drawing Sheets

U.S. PATENT DOCUMENTS

| | | | | |
|---|---|---|---|---|
| 4,648,888 A | * | 3/1987 | Rowland | 95/8 |
| 4,759,848 A | | 7/1988 | Segura et al. | |
| 4,857,086 A | * | 8/1989 | Kawai | 96/111 |
| 5,428,555 A | | 6/1995 | Starkey et al. | |
| 5,989,312 A | * | 11/1999 | Barnhard et al. | 95/8 |
| 6,119,480 A | | 9/2000 | Germain et al. | |
| 6,232,204 B1 | * | 5/2001 | Lorimer et al. | 96/112 |
| 6,361,696 B1 | * | 3/2002 | Spiegelman et al. | 95/8 |
| 6,451,210 B1 | * | 9/2002 | Sivavec et al. | 95/8 |
| 6,537,347 B2 | * | 3/2003 | Motouji et al. | 95/8 |
| 6,773,582 B2 | * | 8/2004 | Anthony | 95/8 |
| 2004/0216609 A1 | * | 11/2004 | Baksh et al. | 95/8 |

FOREIGN PATENT DOCUMENTS

| | | | |
|---|---|---|---|
| EP | 0 977 980 B1 | | 4/1998 |
| EP | 0 932 007 A1 | | 1/1999 |
| FR | 2 728 803 | | 1/1995 |
| FR | 2 735 381 | * | 12/1996 |
| FR | 2 774 006 | | 1/1998 |
| JP | 8-285738 | * | 11/1996 |
| WO | WO 98 48259 | | 4/1998 |

* cited by examiner

METHOD OF GUARANTEEING AT LEAST ONE CHARACTERISTIC OF A FLUID USED FOR PRODUCING FOOD PRODUCTS

BACKGROUND

The present invention relates to a method for guaranteeing at least one characteristic of a fluid used for producing food products.

The requirements in terms of safety and quality are becoming increasingly important in the food industry.

Thus, it seems to be desirable to guarantee that certain characteristics of the fluids used for producing food products possess acceptable values. These characteristics are, for example, characteristics relating to the content of chemical, physical or biological impurities.

The fluids to which the invention relates may be used as technological auxiliary and are therefore not involved in or do not come into contact with the finished food products up to the moment of their consumption. They are, for example, cryogenic fluids used for cooling the food products.

Such fluids may also be used as additives or as ingredients, and they therefore remain in or in contact with the finished food products. These are, for example, fluids used as propellents or for forming protective atmospheres or for modifying the pH.

EP-932 007 discloses a method of filtering, in liquid phase, a cryogenic fluid in order to remove microorganisms and/or physical particles. The cryogenic fluid is, for example, used in the agri-food industry. This filtration method does not include a step of measuring a characteristic of the cryogenic fluid.

U.S. Pat. No. 4,759,848 discloses a method of sterilizing a cryogenic liquid by filtration. This method too does not include a step of measuring a characteristic of the cryogenic liquid.

FR-2 728 803 discloses a method of delivering dry air comprising steps of purifying compressed air, but no step of measuring a characteristic of this air.

WO-98/48259 discloses an in-line method for quantitatively and qualitatively differentiating between biotic and abiotic particles in a gas. This method can be used in the food industry.

U.S. Pat. No. 5,428,555 discloses a system for obtaining and analyzing information relating to a method of producing semiconductor chips using a gas. That document does not mention the step of measuring a characteristic of the gas.

EP-584 747 discloses the use of high-purity helium for producing products. A purity measurement is carried out downstream of the purification devices that are connected in parallel and contain desiccants, adsorbents and/or oxidation catalysts. Such a measurement is used to determine whether the helium has to pass via one or other or via both devices in order to ensure satisfactory purification. Helium is not a fluid used for producing food products, but it can be used as a tracer for any leaks in a package. The method described is also not suitable for such production, as it does not guarantee that the products have been produced with a fluid, at least one characteristic of which complies with a predetermined constraint.

Thus, none of these documents provides a method for guaranteeing at least one characteristic of a fluid used for producing food products.

It is an object of the invention to solve this problem.

This is because it should be pointed out that although the quality of the gases delivered by the gas producer and/or supplier is usually guaranteed, on the other hand no guarantee or no systematic control of the quality of the gases from the chemical, physical and/or microbiological standpoint is provided at the point of use. The influence of the system on the quality of the gas is not monitored, and likewise the constancy over time of the quality of the gases at the point of use is not checked.

The generalized use of HACCP methods in food companies requires users to establish critical control points where risks (of a microbiological, physical or chemical nature) may arise. The quality of the gases at the point of use is therefore a critical point to be controlled within the context of this approach so as to ensure that the gas in contact with the food is not a source of contamination.

The object of the present invention is to formulate an overall approach for controlling and/or guaranteeing the quality of the gases or of the gas mixture from production to the point of use from the microbiological, physical and chemical standpoint.

It is preferable to include the setting up of measures for removing chemical, physical and/or microbiological contaminants at the point of use, the setting-up of a control system for checking the quality of the gases or of the gas mixture right up to the point of use, the setting-up of a continuous recording system for archiving the information (measurements, maintenance operations, failures) that occur along the gas delivery line and the setting-up of a traceability system for linking the delivery of the gases with the customer's production batches.

SUMMARY

For this purpose, the subject of the invention is a method for guaranteeing at least one characteristic of a fluid used for producing food products, characterized in that it comprises the steps of:

providing a system for piping and delivering the fluid, combined with means for producing the products, in order to use the fluid for producing the products;

measuring a value of the characteristic;

comparing the measured value with a predetermined threshold value;

executing an action if the measured value departs from the threshold value;

combining the measured value with first information for identifying at least one product; and storing the associated value and the associated information.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein.

DESCRIPTION OF PREFERRED EMBODIMENTS

In particular embodiments, the method may include one or more of the following features, taken individually or in any technically possible combination:

the action comprises a step of issuing an alarm signal;
the action comprises at least one step carried out on at least one part of the system;
the action comprises a step of cleaning and/or sterilizing at least one part of the system;
the action comprises a step of removing one part of the system and then replacing the removed part with a new part;
the action comprises a step of substituting one part of the system with another part of the system;
said part of the system is a source of the fluid;
the action comprises a step of stopping the delivery of the gas;
the system comprises a device for purifying the fluid, in that said characteristic is a characteristic relating to the purity and the value of the characteristic is measured downstream of the purification device;
the feature relates to the content of a physical, chemical or microbiological impurity;
the first identification information is intermediate and temporal identification information;
the first identification information is delivered by a first clock and it furthermore includes a step of associating second, intermediate and temporal, identification information delivered by a second clock with third, final identification information; and
the first identification information is final identification information.

Figure 1:
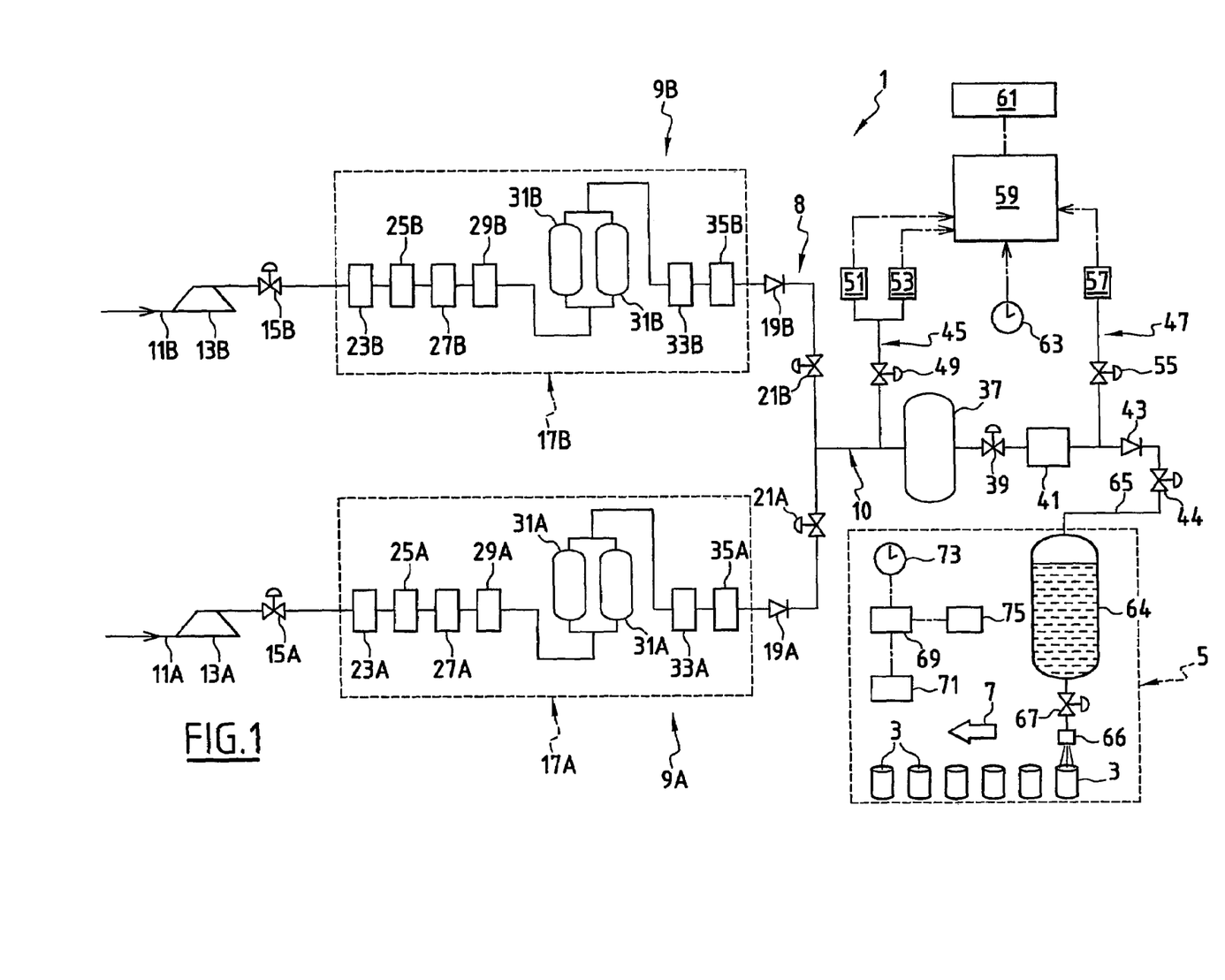
FIG. 1 is a schematic view of a plant in accordance with a first illustrative embodiment of the invention.

FIG. 1 illustrates schematically a plant 1 for producing products 3 using compressed air as technological auxiliary. More specifically, the products 3 are produced by production means 5 which ensure, for example, in-line production as illustrated by the arrow 7 in FIG. 1.

The plant 1 includes a compressed-air piping and delivery system 8. This system 8 comprises two upstream air piping lines 9A and 9B connected to a downstream air piping line 10, which is itself connected to the production means 5.

Since the structures of the lines 9A and 9B are similar, the same numerical references will be used, but followed either by the suffix A in the case of the line 9A or the suffix B in the case of the line 9B. For the same reason, only the structure and the operation of the line 9A will be described in detail below.

The line 9A comprises, in succession from the upstream end to the downstream end:

a line 11A for communication with the ambient atmosphere, which forms the source of air;
an air compressor 13A;
a valve 15A;
a purification unit 17A;
a nonreturn valve 19A; and
a valve 21A.

The purification unit 17A comprises, in succession from the upstream to the downstream end:

a cyclone filter 23A;
a prefilter 25a for removing particles having a size larger than 25 μm;
a submicron filter 27A for removing particles having sizes of greater than 0.1 μm, for example a coalescing filter;
a submicron filter 29A for removing particles having dimensions of larger than 0.01 μm, for example a coalescing filter;

two desiccators 31A placed in parallel and each comprising a container filled with an adsorbent, such as alumina;
an active-carbon filter 33A; and
a dust filter 35A, for example a filter made of sintered material.

It should be noted that the various elements of the upstream line 9A are conventional elements.

The downstream line 10 comprises, in succession from the upstream end to the downstream end:

a buffer tank 37;
a valve 39;
a bacteriological filter 41, for example a hydrophobic pleated-membrane filter;
a nonreturn valve 43; and
a valve 44.

These various elements are also conventional elements.

The downstream line 10 is connected upstream of the tank 37 to a first branch line 45 and, between the bacteriological filter 41 and the nonreturn valve 43, to a second branch line 47. The branch line 45 is provided with a valve 49 and is connected in parallel to a sensor 51 for measuring the water or moisture content and to a sensor 53 for measuring the CO and $CO_2$ content. These sensors are also conventional elements.

The second branch line 47 is provided with a valve 55 and is connected to a sensor 57 for measuring information relating to the microbiological purity, for example a sensor capable of determining the content of biotic particles as described in WO-98/48259.

The plant 1 furthermore includes an electronic data processing unit 59 and, connected to this unit 59, are a memory 61 and a clock 63. The unit 59 comprises in particular a microprocessor suitably programmed to ensure that the operations described below are carried out. Moreover, the sensors 51, 53 and 57 are connected to the unit 59 in order to deliver to it information relating to the characteristics or quantities that they measure.

The production means described below will, for example, be means for producing containers 3 for containing milk. They could also be containers for containing a dessert cream. The description of these means 5 will be limited to elements needed for the description of the invention and will therefore be very schematic, the rest of these means 5 being moreover conventional.

The means 5 include a tank 64 containing milk. The top of this tank 64 is connected to the downstream section 65 of the line 10. The tank 64 feeds, via its bottom, means 66 for filling the containers 3. A valve 67 is placed between the bottom of the tank 64 and the filling means 66.

The production means 5 furthermore include an electronic data processing unit 69 and, connected to this unit, are means 71 for providing the products 3 with final identification information, for example a batch number, a clock 73 synchronized with the clock 63, and a memory 75. The unit 69 comprises in particular a microprocessor suitably programmed for ensuring that the operations described below are carried out.

The operation of the plant 1 is as follows. The valves 15A and 21A are open, whereas the valves 15B and 21B are closed.

Air from the external atmosphere is piped via the line 11A, compressed by the compressor 13A and then undergoes pre-desiccation in the filter 23A, making it possible to remove about 96% by weight of the water contained in the air. Next, the filters 25A, 27A and 29A remove most of the hydrocarbons that the air may contain, and especially the oils. Typically, the oil content of the air output by the filter 29A is less than 0.01 ppm.

The air then passes through one of the desiccators 31A in which it is desiccated by an adsorption process. The other desiccator 31A is then in regeneration phase, by elution as is conventional, for example using a stream of dry air taken off as output from the buffer tank 37. Typically, the dew point of the air output by the desiccator 31A used is −40° C. or below.

The desiccated air then passes through the filter 33A where the last traces and odors of oil are substantially removed (the residual content is about 0.003 ppm) and then the filter 35A, which removes the dust contained in the air.

The air leaving the unit 17A contains, per $m^3$, fewer than 3520 particles having a size greater than or equal to 0.5 μm (ISO Class 5 according to the classes defined by ISO 14644-1). The moisture content of the air is then less than 0.05% and its hydrocarbon content is less than 100 μl/l (0.09 $mg/m^3$).

The air thus compressed, desiccated, dedusted and deoiled is then sent to the buffer tank 37.

The valve 39 is opened to withdraw air from the tank 37. The microorganisms present in this air are removed by the filter 41. Since the valve 44 is open, the air thus compressed and purified is delivered to the top of the tank 64 via the downstream section 65 of the line 10. The compressed air therefore pushes the milk to the bottom of the tank 64, expelling it from the tank 64 and therefore filling the containers 3.

The products 3 are thus produced by means of the compressed and purified air delivered solely by the line 9A and the line 10, the line 9B not being used.

During this production run, the valves 49 and 55 of the branch lines 45 and 47 are open in order to allow the sensors 51, 53 and 57 to make, and deliver to the unit 59:
- a measurement of the moisture content of the air used for producing the products 3;
- a measurement of the CO and $CO_2$ content of the air used, this content being a tracer of a possible drift in the oil content of the air used to produce the products 3; and
- a measurement of the content of biotic particles, this content being representative of the content of microbiological impurities of the air used to produce the products 3.

These various items of information transmitted to the unit 59 are associated therein with temporal information delivered by the clock. 63. This time-associated information is then stored in the memory 61. Thus, this stored information makes it possible to determine, for a given instant, or for a given time period, the purity, in terms of moisture, $CO/CO_2$ content and microbiological impurity content, of the air used for producing the products 3.

Similarly, the electronic data processing unit 69 associates the final information for identifying the products 3, which are delivered by the means 71, with temporal information delivered by the clock 73, and the final information is stored in the memory 75. Thus, for given products 3, it is possible to known the instant, or the time period, when they were produced.

Since the plant 1 shown in FIG. 1 records the information about the purity of the air used for producing the products 3, it is possible to check that this production was carried out under satisfactory safety and quality conditions.

Moreover, the user of the plant 1 is capable of proving that given products 3 were produced using air of satisfactory purity.

This is because it is possible, for given products 3, to known at what instant, or during which time period, they were produced, thanks to the information stored in the memory 75. This temporal information therefore makes it possible, thanks to the information stored in the memory 61, to determine the information regarding the purity of the air used at that instant, or during that time period. It should be noted that the temporal information delivered by the clocks 63 and 73 constitutes intermediate identification information. Furthermore, it should be noted that one and the same clock can be used instead of these two clocks to deliver the same intermediate identification information to the units 59 and 69.

The plant 1 therefore makes it possible to implement traceability and quality procedures for meeting the enhanced safety requirements in the food sector.

The electronic data processing unit 59 may furthermore be designed to command the closing of the valves 15A and 21A on the one hand, and the opening of the valves 15B and 21B on the other, so that the air is compressed and purified, upstream of the tank 37, by the line 9B rather than by the line 9A. This command may be issued as soon as the unit 59 determines, by comparison, that the water or oil content has exceeded a respective predetermined threshold value stored in the memory 61. Thus, the unit 59 may selectively command the lines 9A and 9B to be connected to the line 10 so as to guarantee the quality of the air used for producing the products 3.

More generally, the purity information received by the unit 59 may be used to carry out various actions on the lines 9A, 913 and 10, so as to correct the observed purity defects.

It should also be noted that the plant 1 may comprise only a single upstream line 9 (another variant may be the use of a single means of communication with a fluid source, namely the use of a single compressor connected to the two purification lines 9A and 9B).

Figure 2:
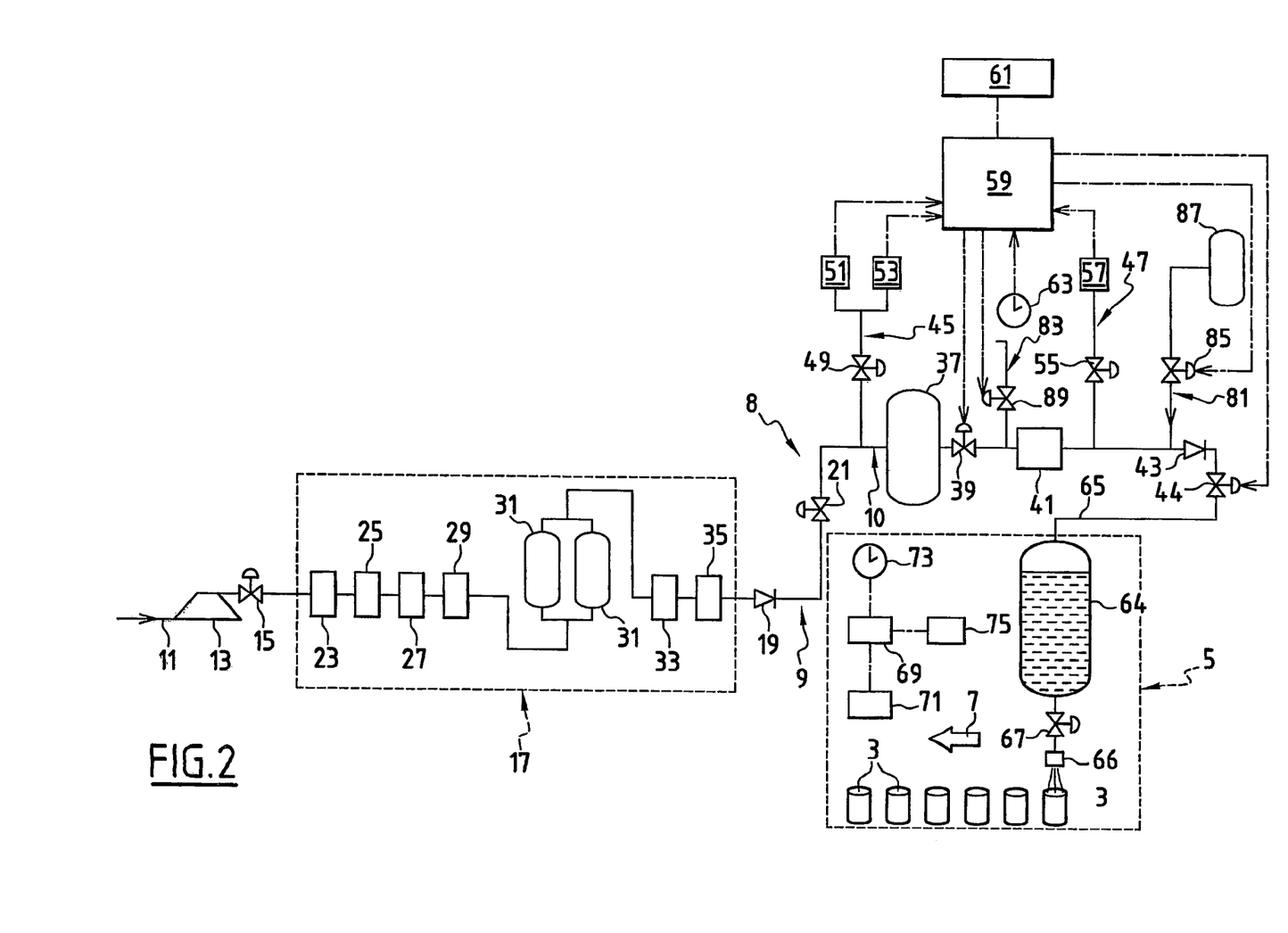
FIG. 2 is a schematic view of a variant of the plant shown in FIG. 1.

Thus, FIG. 2 illustrates a variant of the plant 1 that is distinguished from that described above by the fact that the system 8 comprises only one upstream line 9. The downstream line 10 is provided with a third branch line 81 located between the branch line 47 and the nonreturn valve 43 and with a fourth branch line 83 located between the valve 39 and the filter 41.

The branch line 81 is provided with a valve 85 and is connected to a source 87 of a cleaning and/or sterilizing fluid, for example STEROXAL (registered trade mark) sold by L'Air Liquide, or a source of vapor.

The branch line 83 is vented at its opposite end to that connecting it to the downstream line 10. However, it should be noted that it could be connected to the line 81 so as to allow the cleaning and/or sterilizing fluid used to be recycled.

When the unit 59 determines, by comparison, that the microbiological impurity content information delivered by the sensor 57 is greater than a predetermined threshold value stored in the memory 61, the unit 59 then causes the valves 39 and 44 to be closed and the valves 85 and 89 to be opened.

The fluid in the reservoir 87 then passes through the filter 41, which sterilizes it, and is then vented via the line 83. This cleaning and/or sterilizing operation is continued for a predetermined time and then the unit 59 causes the valves 85 and 89 to be closed and the valves 39 and 44 to be opened.

Thus, the unit 59 is designed to clean and/or sterilize the line 10 should it be necessary, thereby making it possible even more significantly to guarantee the quality of the air used for producing the products 3.

It should be noted that the sensor 57 may be replaced with a device for taking off discrete samples of gas, which may be analyzed in terms of microbiological contamination by a laboratory located on a site away from that of the plant 1. The microbiological purity information delivered by the laboratory is associated, together with the purity information delivered by the sensors 51 and 53, with the temporal information delivered by the clock 63. The information thus associated is stored in the memory 61.

The principles of purification, acquisition of purity-related information and recording of this information may be applied to all types of gases or even of fluids used in the production of products. In particular, the fluid used for producing the products may be delivered in liquid form.

Figure 3:
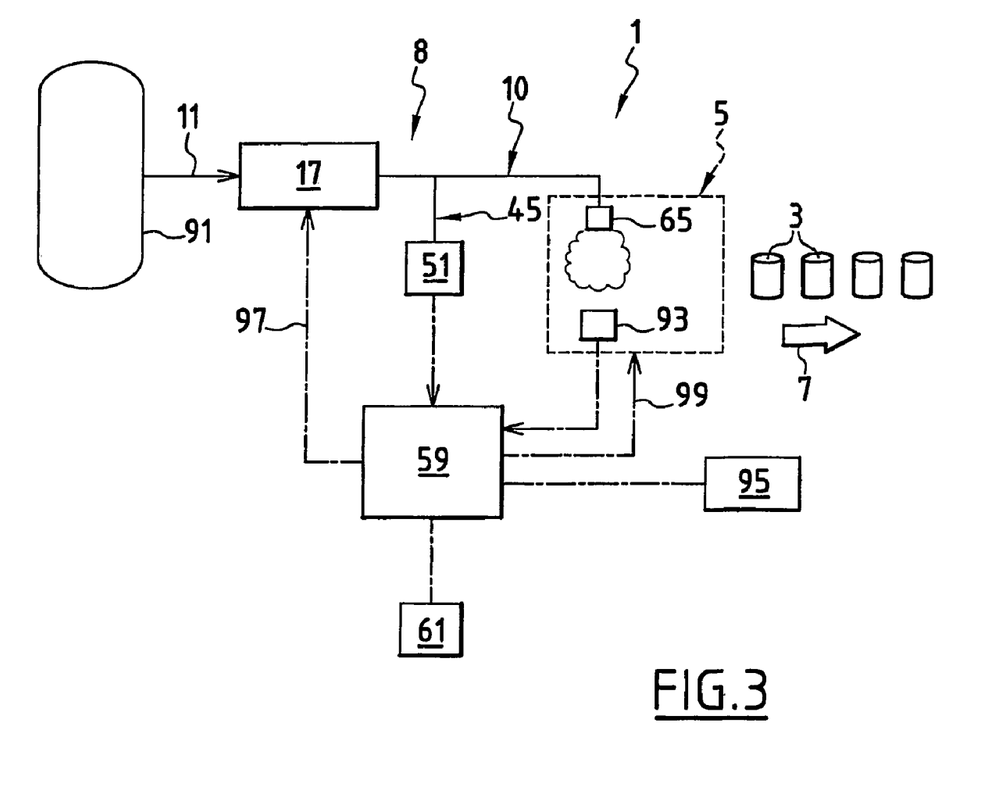
FIG. 3 is a schematic view of a plant in accordance with a second illustrative embodiment of the invention.

FIG. 3 thus illustrates a general form of the invention in which the system 8 comprises, from the upstream end to the downstream end, a storage tank 91, for example for storing, in liquid form, a fluid to be delivered, a line 11, a purification unit 17, a line 10 and means 65 for delivering, for example in gaseous form as in the examples of FIGS. 1 and 2, the purified fluid. These means 65 are associated with means 5 for producing products 3.

A sensor 51 makes it possible, thanks to a branch line 45, to measure a characteristic relating to the purity of the fluid downstream of the purification unit 17. This sensor 51 transmits this information to the electronic data processing unit 59, which also receives final information, delivered by identification means 93, for identifying the products 3. The purity information delivered by the sensor 51 and the product identification information delivered by the means 93 are combined by the unit 59 and then stored in the memory 61 so as to make it possible to determine, in respect of given products 3, what was the purity information acquired by the sensor 51 for the fluid used for producing these products 3.

This information combined by the unit 59 may also be sent via a remote communication device 95, such as a modem, to a monitoring installation away from the site of the plant 1.

As illustrated by the arrows 97 and 99, the unit 59 may also be designed to act on the purification unit 17 or on the means 5 for producing the products 3 according to the information received by the sensor 51.

This may, for example, involve initiating a step of cleaning and/or sterilizing the lines 10 and 11 and/or the unit 17, when the unit 59 determines, by comparison, that the value measured by the sensor 51 exceeds a predetermined threshold value stored in the memory 61.

In general, the unit 17 may be a unit designed to eliminate physical impurities, such as dust, chemical impurities, such as water, or microbiological impurities, such as bacteria.

In the example shown in FIG. 3, the combining of the information delivered by the sensor 51 with the final information for identifying the products 3 makes it possible to correlate the purity information with the products 3 so as to use intermediate identification information, such as temporal information delivered by a clock.

It should be noted that the correlation of the information delivered by the sensor 51 with the products 3, including via temporal information, is not absolutely essential, just the storage in the memory 61 of the information delivered by the sensor 51 making it possible to prove that safety and quality conditions have indeed been met during production of at least certain products 3.

It should also be noted that the unit or units or purification devices will in general be placed downstream of critical sections of the system 8. Moreover, it is preferable to place the purity measurement sensor or sensors as close as possible to the fluid delivery means 65.

Figure 4:
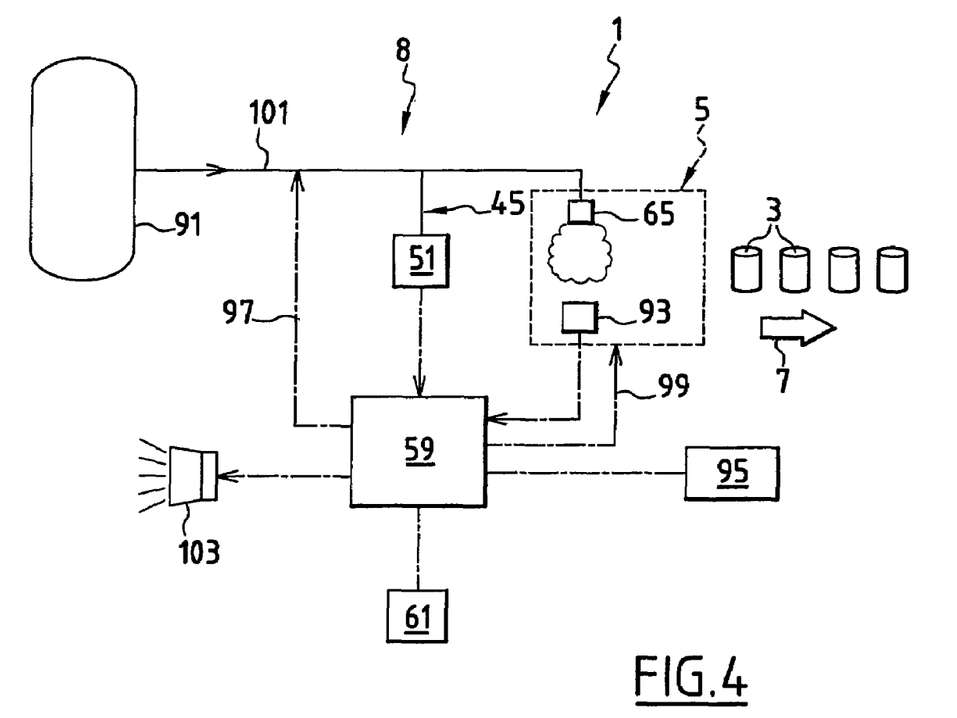
FIG. 4 is a schematic view of a plant in accordance with a third illustrative embodiment of this invention.

FIG. 4 illustrates in general a plant 1 dedicated to the production of food products 3. Thus, the system 8 is made up from elements specifically designed for the food industry and making it possible in particular to limit the risks of chemical, physical and microbiological contamination. Furthermore, the plant is distinguished by what follows from that of FIG. 3.

The system 8, the structure of which has not been shown in detail in FIG. 4, may comprise all types of elements, and especially purification units or devices, although this is not absolutely essential, unlike the case of FIG. 3.

The sensor 51 measures a value of a characteristic of the fluid, which may, although this is not necessary, be related to its purity. Thus, this characteristic may be a physical, chemical or biological impurity content, but it may also be the temperature, the pressure, etc.

The electronic data processing unit 59:
compares the value measured by the sensor 51 with a predetermined threshold value stored in the memory 61, which corresponds to a value that it is desired to guarantee in respect of the characteristic;
associates the values delivered by the sensor 51 with final identification information delivered by the identification means 93 so as to correlate each measured value with the product(s) 3 produced by the use of the fluid with the feature having the measured value; and
stores the values, and the information thus associated, in the memory 61.

Should the measured value exceed the predetermined threshold value, the electronic unit 59 is furthermore designed to initiate the execution of actions.

Some of these actions may be carried out on at least a part 101 of the piping and delivering system 8, as illustrated by the arrow 97. This may, for example, be the removal of the part 101 and its replacement by a new part 101.

This may also be the substitution of a part of the system 8 for another part, in order to pipe and deliver the fluid, as was described with regard to FIG. 1 for substituting the upstream line 9B for the upstream line 9A. In this case, the action is executed by the unit 59.

The action may also be to stop the delivery of the fluid, by closure of a valve of the system 8 by the unit 59, or to remove the source 91 and replace it with a new source 91.

Actions may also be carried out by the unit 59 on the means 5 for producing the products 3, as illustrated by the arrow 99. For example, these production means 5 may then be shut down after making the fluid delivery line safe (by stopping the supply of fluid).

Furthermore, one action may be the generation of an alarm signal by a device 103.

This signal may, as shown schematically in FIG. 4, be an audible signal emitted by a loud speaker, but it may also be an optical signal emitted, for example, by a monitoring screen.

The plant 1 therefore makes it possible to execute corrective measures after detecting the non-compliance of constraints imposed on the characteristic of the fluid.

Furthermore, associating the measured values with information for identifying the products, and the subsequent storage in the memory 61 of the information, makes it possible to check a posteriori what was the value of the characteristic of the fluid used for the production of certain products 3.

Thus, the plant 1 makes it possible to implement traceability procedures, and contributes even more to guaranteeing that the characteristic of the fluid used does indeed comply with certain predetermined constraints. It should be noted that the threshold value may be a maximum value to be respected or a minimum value to be respected. Thus, the electronic unit 59 can initiate the execution of the various actions when the measured value exceeds the threshold value or when it falls below the threshold value.

Finally, it should be noted that the measured values may be associated not with final identification information but with intermediate identification information, for example temporal information delivered by a clock as described with regard to FIGS. 1 and 2.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

The invention claimed is:

1. A method for guaranteeing at least one characteristic of a fluid used for producing food products, comprising:
   a) providing a system for piping and delivering the fluid, combined with means for producing the products, in order to use the fluid for producing the products;
   b) measuring a value of the characteristic;
   c) comparing the measured value with a predetermined threshold value;
   d) executing an action if the measured value departs from the threshold value;
   e) combining the measured value with first information for identifying at least one product; and
   f) storing the combined measured value and first information.

2. The method of claim 1, wherein said action comprises issuing an alarm signal.

3. The method of claim 1, wherein said action comprises at least one step carried out on at least one part of the system.

4. The method of claim 3, wherein said action comprises a step of cleaning and sterilizing at least one part of the system.

5. The method of claim 3, wherein said action comprises a step of removing one part of the system and then replacing the removed part with a new part.

6. The method of claim 3, wherein said action comprises a step of substituting one part of the system with another part of the system.

7. The method of claim 5, wherein said part of the system is a source of the fluid.

8. The method of claim 6, wherein said part of the system is a source of the fluid.

9. The method of claim 7, wherein said action comprises a step of stopping the delivery of the fluid.

10. The method of claim 7, wherein said system competes a device for purifying the fluid, wherein said characteristic is a characteristic relating to the purity, and the value of the characteristic is measured downstream of the purification device.

11. The method of claim 10, wherein said characteristic relates to the content of a physical, chemical, or microbiological impurity.

12. The method of claim 1, wherein the first identification information is intermediate and temporal identification information.

13. The method of claim 12, wherein said first identification information is delivered by a first clock, and further compulsion a step of associating second, intermediate and temporal, identification information delivered by a second clock with third, final identification information.

14. The method of claim 13, wherein said first identification information is final identification information.

* * * * *

UNITED STATES PATENT AND TRADEMARK OFFICE
CERTIFICATE OF CORRECTION

PATENT NO. : 7,393,380 B2  Page 1 of 1
APPLICATION NO. : 10/497931
DATED : July 1, 2008
INVENTOR(S) : Jean-Francois Vie et al.

It is certified that error appears in the above-identified patent and that said Letters Patent is hereby corrected as shown below:

In Column 10, line 10, replace the word "competes" with the word --comprises--.

In Column 10, line 23, replace the word "compulsion" with the word --comprising--.

Signed and Sealed this

Twentieth Day of April, 2010

David J. Kappos
*Director of the United States Patent and Trademark Office*